United States Patent
Faccioli et al.

[11] Patent Number: 6,024,745
[45] Date of Patent: Feb. 15, 2000

[54] EXTERNAL MINISPLINT DEVICE

[75] Inventors: Giovanni Faccioli, Monzambano; Daniele Venturini, Povegliano Veronese, both of Italy

[73] Assignee: Orthofix, S.r.l., Italy

[21] Appl. No.: 09/082,225

[22] Filed: May 20, 1998

[30] Foreign Application Priority Data

May 21, 1997 [IT] Italy ................................. VR97A0042

[51] Int. Cl.⁷ .................................................. A61B 17/60
[52] U.S. Cl. .................................. 606/54; 606/57; 606/59
[58] Field of Search ................................. 606/54, 55, 56, 606/57, 58, 59, 105

[56] References Cited

U.S. PATENT DOCUMENTS

| Re. 31,809 | 1/1985 | Danieletto et al. | 128/92 A |
|---|---|---|---|
| 2,391,537 | 12/1945 | Anderson | 128/84 |
| 4,312,336 | 1/1982 | Danieletto et al. | 128/92 A |
| 4,502,473 | 3/1985 | Harris et al. | 128/92 A |
| 4,554,915 | 11/1985 | Brumfield | 128/92 A |
| 4,621,627 | 11/1986 | DeBastiani et al. | 128/92 ZZ |
| 4,643,177 | 2/1987 | Sheppard et al. | 128/84 C |
| 4,988,349 | 1/1991 | Pennig | 606/58 |
| 5,019,077 | 5/1991 | De Bastianni et al. | 606/54 |
| 5,160,335 | 11/1992 | Wagenknecht | 606/59 |
| 5,207,676 | 5/1993 | Canadell et al. | 606/54 |
| 5,292,322 | 3/1994 | Faccioli et al. | 606/59 |
| 5,304,177 | 4/1994 | Pennig | 606/58 |
| 5,320,622 | 6/1994 | Faccioli et al. | 606/58 |
| 5,342,360 | 8/1994 | Faccioli et al. | 606/59 |
| 5,454,810 | 10/1995 | Pohl et al. | 606/59 |
| 5,591,164 | 1/1997 | Nazre et al. | 606/59 |
| 5,709,681 | 1/1998 | Pennig | 606/54 |
| 5,728,096 | 3/1998 | Faccioli et al. | 606/54 |
| 5,769,851 | 6/1998 | Veith | 606/57 |

FOREIGN PATENT DOCUMENTS

| 0011258 | 11/1979 | European Pat. Off. | A61B 17/18 |
|---|---|---|---|
| 2557933 | 1/1984 | France | F16B 9/02 |
| 3722595 | 1/1989 | Germany | A61B 17/60 |
| 8802463 | 5/1990 | Netherlands | A61B 17/60 |
| 8909031 | 10/1989 | WIPO | A61B 17/60 |
| 9007305 | 7/1990 | WIPO | A61B 17/60 |
| 9111150 | 8/1991 | WIPO | A61B 17/60 |
| 9111151 | 8/1991 | WIPO | A61B 17/60 |
| 9423662 | 10/1994 | WIPO | . |

OTHER PUBLICATIONS

Orthofix Srl., "ORTHOFIX® The Pennig Dynamic Wrist Fixator, Operative Technique", Mar. 25, 1992, 47 pages.

(List continued on next page.)

*Primary Examiner*—Michael Buiz
*Assistant Examiner*—Daphna Shai
*Attorney, Agent, or Firm*—Hopgood, Calimafde, Kalil & Judlowe

[57] ABSTRACT

An external minisplint device comprises an elongated body (2; 2'; 2"; 2'''; 2$^{iv}$; 101, 102) supporting at least one pair of clamps (3, 4; 3', 4'; 3", 4"; 3''', 4'''; 3$^{iv}$, 4$^{iv}$; 103, 104) each of which is capable of securing at least one pair of transverse bone bolts (F, F', F", F''', F$^{iv}$, F1). A longitudinal guide (5; 5'; 5"; 5'''; 5$^{iv}$; 105, 106) associated with the elongated body guides the longitudinal translational movement of at least one of the clamps (4; 4'; 4"; 4'''; 4$^{iv}$; 103, 104). The minisplint device further comprises at least one longitudinal adjustment screw (6; 6'; 6"; 6'''; 6$^{iv}$; 107, 108) which can rotate within the elongated body and which engages a corresponding threaded hole (13; 13'; 13"; 13'''; 13$^{iv}$; 135, 136) formed in the clamp capable of translational motion for selectively positioning it along the longitudinal guide. The screw has a head (7; 7'; 7"; 7'''; 7$^{iv}$; 111, 112) which partly projects from the end of the elongated body. The adjustment screw is axially imobilized when it is rotated. The axial immobilizer comprises at least one smooth key, and preferably a pair of smooth gauged keys (16, 16.1; 16', 16.1'; 16", 16.1"; 16''', 16.1'''; 16$^{iv}$, 16.1$^{iv}$; 109, 109.1, 110, 110.1) insert in the elongated body in tangential contact with the base of a circular groove (17; 17'; 17"; 17'''; 17$^{iv}$; 124, 125) formed in the head (7; 7'; 7"; 7'''; 7$^{iv}$; 111, 112) of the adjustment screw (6; 6'; 6"; 6'''; 6$^{iv}$; 107, 108).

20 Claims, 6 Drawing Sheets

OTHER PUBLICATIONS

Pfeil, "Heidelberg External Fixation, Unilateral Fixation Techniques in Limb Deformity Corrections," Georg Thieme Verlag, 1998 Wandrey trans, (1st ed. 1994), 48 pages.

Orthofix Srl., "ORTHOFIX® Modulsystem, General Application Instructions," Jan. 1996, 28 pages.

Orthofix Srl., "ORTHOFIX® Modulsystem", Jul. 1997, prior edition before May 21, 1997, 16 pages.

Saleh, "ORTHOFIX® Modulsystem, Operative Technique, Limb Reconstruction System", Orthofix Srl., Mar. 1998, prior edition before May 21, 1997, 67 pages.

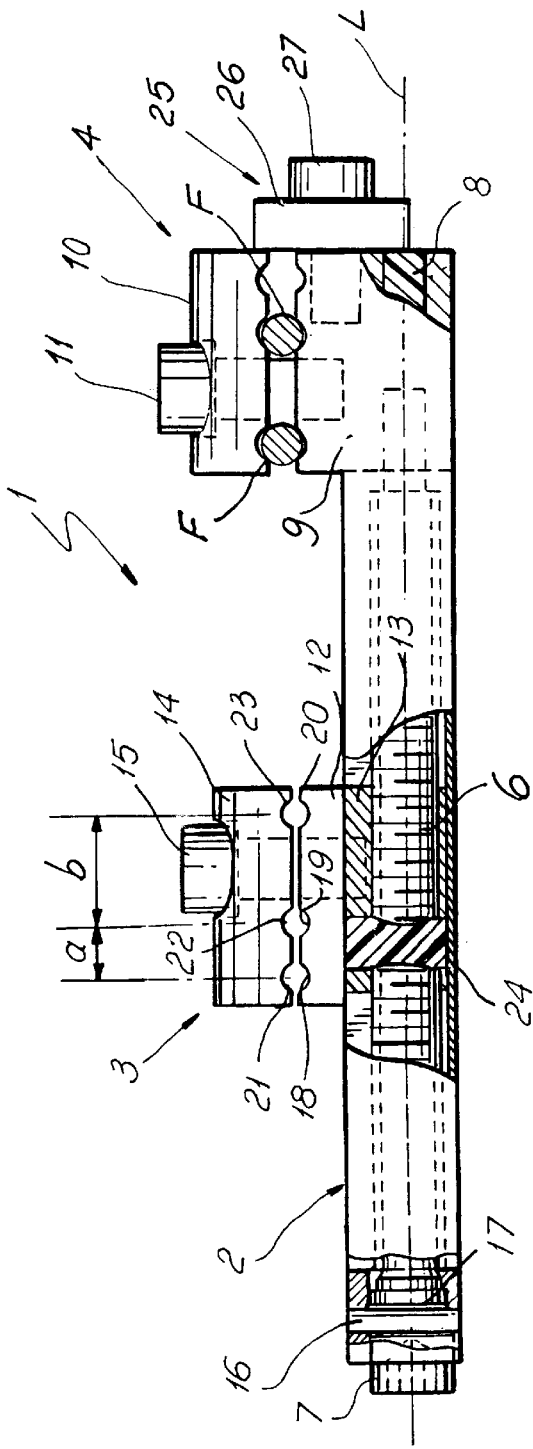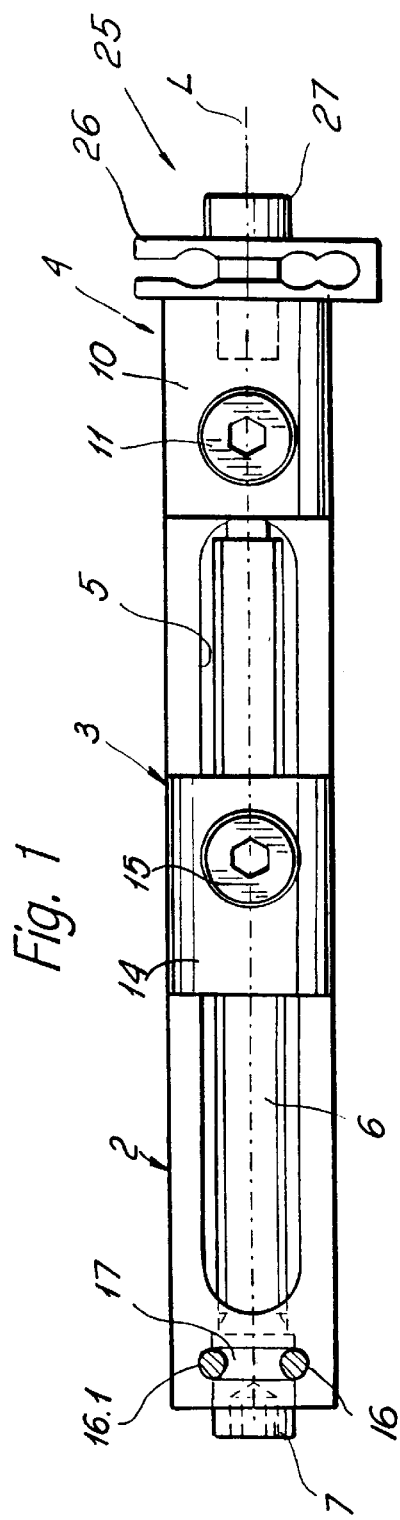

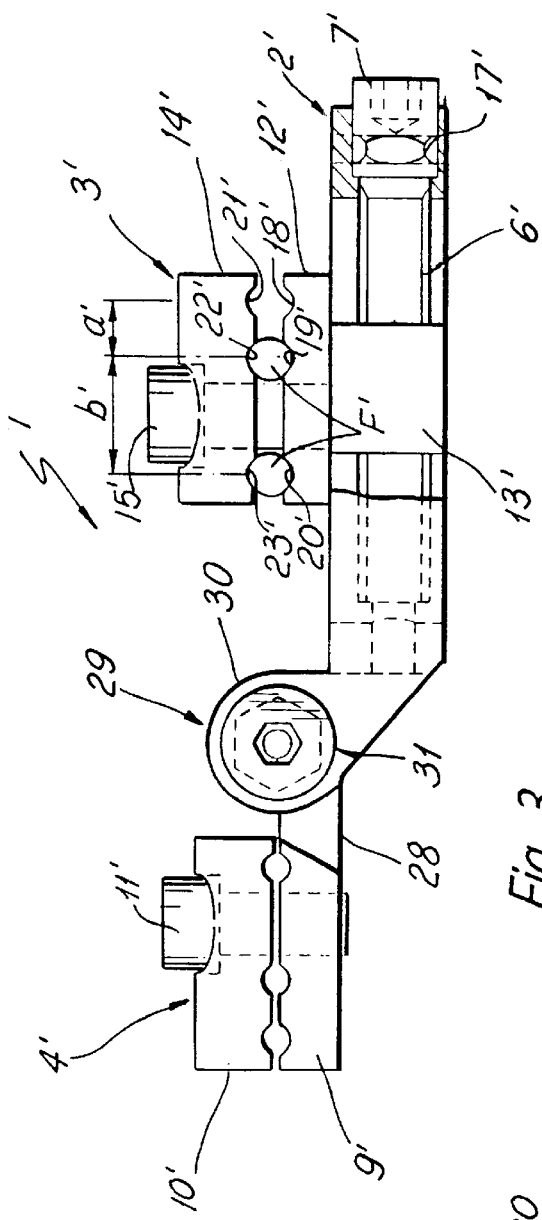
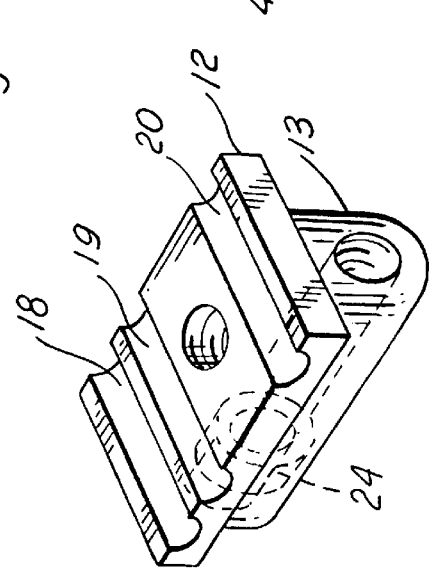
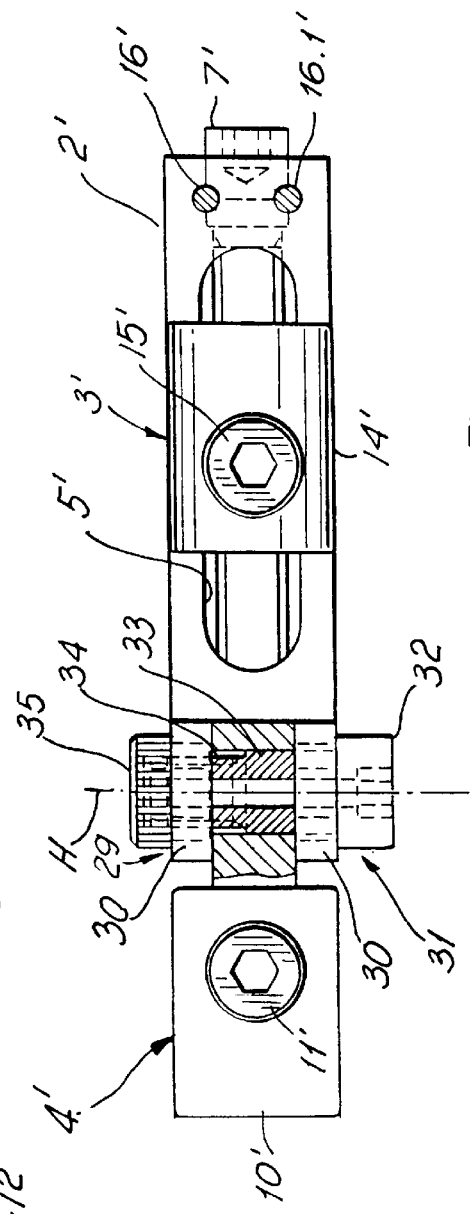
Fig. 3
Fig. 2A
Fig. 4

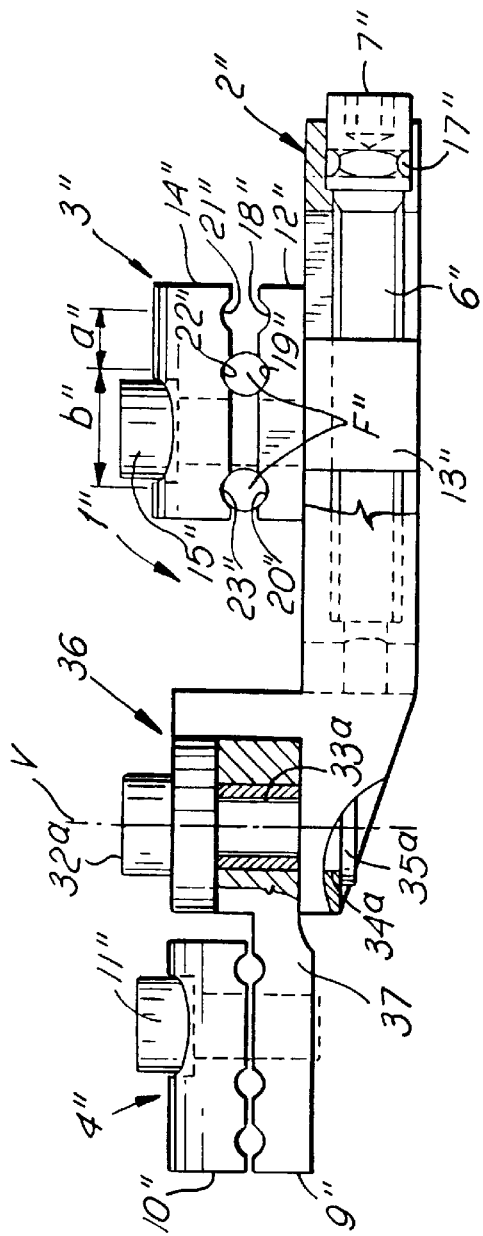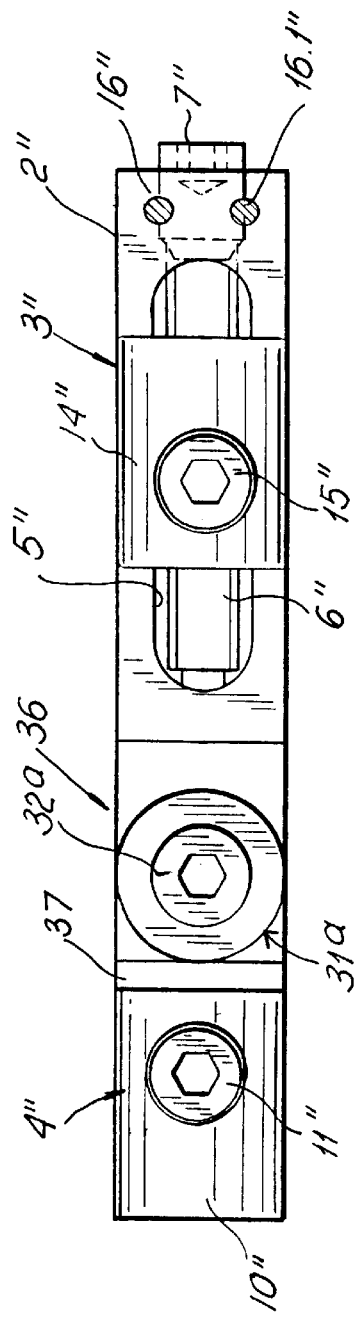

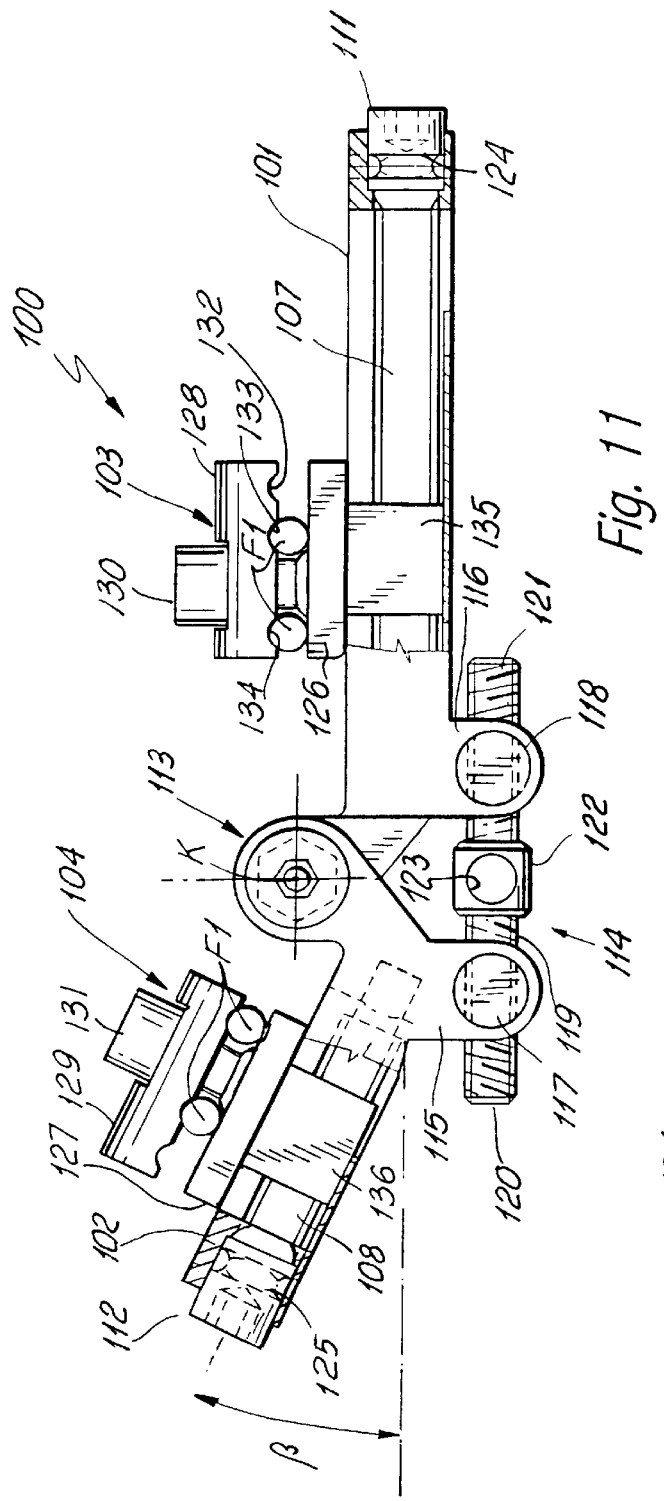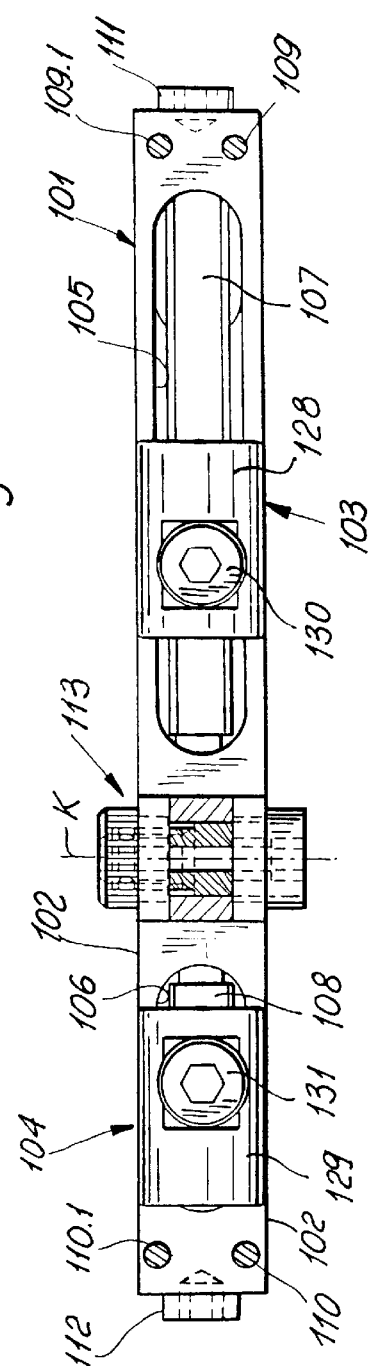
Fig. 11
Fig. 12

EXTERNAL MINISPLINT DEVICE

FIELD OF THE INVENTION

This invention finds application in bone surgery and in the treatment of fractures or deformations of small bones, for example of the hand or foot, or in maxillofacial surgery, and relates in particular to a minisplint of the type which is both fixed and articulated.

BACKGROUND OF THE INVENTION

Compact fixation devices of the above-mentioned type, for example, that of the fixed type described in Italian Patent No. 1,183,736 and that of the articulated type described in U.S. Pat. No. 4,604,997, are known.

These known minisplint devices effectively perform the task required of them but are susceptible of some improvements.

In fact, both the minisplint devices mentioned above have at least one clamp which can move with respect to a longitudinal support by means of an adjustment screw in which the screw is axially immobilized with respect to the by a washer which is retained by one recessed end or by means of a locking pin. However these immobilizing systems have little strength in the axial direction, and can deform or break very easily, and also show excessive play.

Secondly, the clamps have only two seats for the bone bolts which are located symmetrically with respect to a tightening screw, with a minimum distance which may be excessive for small bones, and which in any event is not always an optimum distance.

Furthermore, the opposing half-cylindrical seats formed by the clamps only make it possible to securely hold bolts or Kirschner wires of a single diameter.

Another disadvantage lies in the limitation of the effective travel of the movable clamp due to the fact that the slide of the latter cannot run to the end of the longitudinal guide groove.

Finally, in the case of an articulated clamp, the rotating joint has a fixed limb which is of excessive size on the side of the securing head, and therefore a different device must be used for mounting on each side of the bone. Finally, the relative angle formed between the two parts connected by the joint is adjusted manually and approximately, and not micrometrically.

SUMMARY OF THE INVENTION

The main object of this invention is to avoid or at least diminish the disadvantages described above.

A particular object is to provide an external minisplint device which guarantees reliable, stable and accurate positioning of the movable clamps.

Another object is to provide an external minisplint device by means of which bone bolts of different diameters can be reliably secured at variable minimum distances.

A further object is that of providing a bilateral minisplint, i.e. one which can be readily fitted on both sides of a fracture.

Yet a further object is to provide a minisplint with an axial joint by means of which the angle formed by its rotating parts can be adjusted micrometrically.

These objects and others which will become clearer below are accomplished by a device according to claim 1, characterized in that it provides means for axially immobilizing the adjustment screw comprising at least a smooth gauged key inserted in the clamp support arranged so as to act tangentially together with a circular groove formed towards one end of the adjustment screw.

Preferably the circular groove is formed in the head of the adjustment screw. In addition to this, two gauged keys which are substantially parallel and symmetrical with respect to the adjustment screw may be provided in order to act with opposing parts thereof.

These securing means ensure a high resistance to stresses and minimum play in the axial direction.

Each clamp comprises a base and a cover, which can be coupled together by means of a locking screw, having corresponding transverse seats for at least three longitudinally offset bone bolts.

Advantageously the above-described seats have an approximately semi-elliptical shape in cross-section so that bone bolts of different diameters can be accepted.

Furthermore, one of the above-described seats is located opposite the other two with respect to the locking screw and the distance between the two seats on the same side is less than the distance between the two seats on opposite sides with respect to the locking screw.

The base of each transversely movable clamp has on the underside a key which is able to slide in a longitudinal groove of complementary shape formed in the support in order to provide the guide means.

A threaded hole is constructed in the above-described key or lower appendage which houses an insert of elastomer material. The insert has a central hole the diameter of which is slightly less than that of the adjustment screw, in order to exert an anti-loosening braking effect on the latter when the adjustment screw is screwed through it.

The support may comprise a one-piece bar of substantially rectangular shape at one end of which is provided a projection defining the base of one of the clamps.

At the other end of the bar provision may be made for a spherical joint with means for securing the base of one of the clamps in a predetermined position.

As an alternative, the support may be formed of two terminal bars articulated by means of a central axial joint with a transverse axis of rotation in which a movable pin is provided which can be inserted from either side with respect to the center of the joint in order that the device may be fitted bilaterally.

BRIEF DESCRIPTION OF THE DRAWINGS

Further features and advantages of the invention will become apparent from the detailed description of the invention including some preferred, though not all, embodiments of the minisplint devices according to the invention which are illustrated by way of example and not restrictively through the drawings in which:

FIG. 1 shows a side view of a first embodiment of the minisplint device according to the invention;

FIG. 2 shows a view from above of the minisplint device in FIG. 1;

FIG. 2a is a perspective view of the movable clamp of FIGS. 1 and 2;

FIG. 3 shows a side view of a second embodiment of the minisplint device according to the invention;

FIG. 4 shows a view from above of the minisplint device in FIG. 3;

FIG. 5 shows a side view of a second embodiment of the minisplint device according to the invention;

FIG. 6 shows a view from above of the minisplint device in FIG. 5;

FIG. 11 shows a side view of a fifth embodiment of the minisplint device according to the invention; and FIG. 12 shows a view from above of the minisplint device in FIG. 11.

Corresponding reference characters indicate corresponding parts throughout the several views of the drawings.

DETAILED DESCRIPTION OF THE INVENTION

Figure 7:
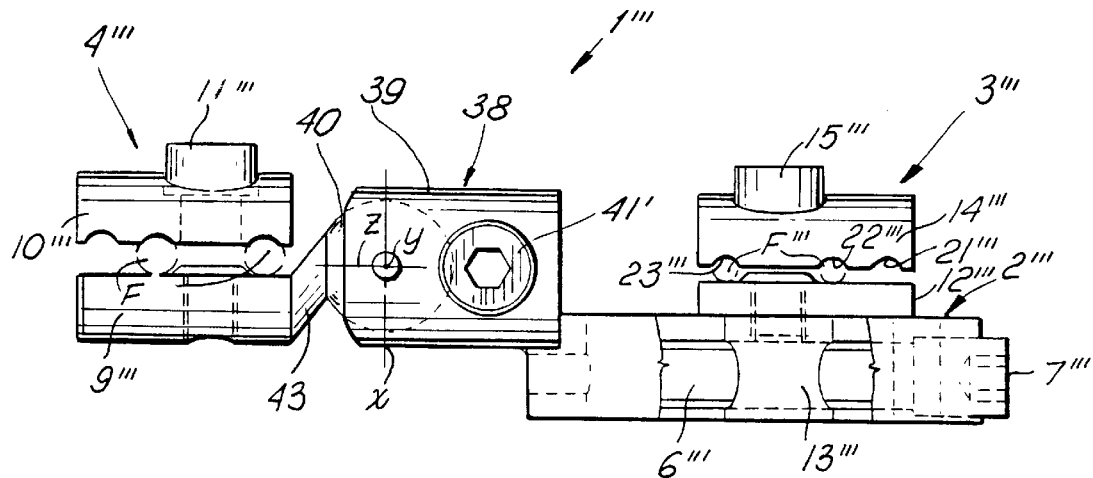
FIG. 7 shows a side view of a third embodiment of the minisplint device according to the invention.

With reference to FIGS. 1 and 2, an external minisplint device according to the invention, indicated as a whole by reference number 1, is illustrated, and essentially comprises an elongated body 2 which supports a pair of clamps 3, 4 for bone bolts F.

Elongated body 2 preferably comprises a parallelepiped-bar of approximately rectangular cross-sectional shape having a longitudinal axis L. Body 2 has a longitudinal groove 5 which extends over a good or substantial part of its length and defines a longitudinal guide means for at least one of the clamps, such as clamp 3.

Clamp 3 can be moved along groove 5 by means of an adjusting or adjustment screw 6 which is rotatably supported in two end holes in body 2 in line with longitudinal axis L. Adjustment screw 6 has a recessed hexagonal head 7 for an Allen key which projects from the end of body 2. The end hole opposite head 7 of screw 6 is closed off by means of a plug 8 of elastomer material to avoid the build-up of impurities and the risk of infections.

Fixed clamp 4 comprises a base 9 which is integral with body 2 and a cover 10 which is connected to base 9 by means of a locking screw 11 which also has a recessed hexagonal head.

Movable clamp 3 also has a base 12 with a depending slide-flange, lower appendage or key 13 of a width slightly less than that of groove 5 so that it can slide freely along it. In lower appendage or key 13 there is a threaded hole which is engaged by adjustment screw 6. The longitudinal ends of key 13 have rounded ends so that they can be inserted into the ends of complementary shape in groove 5 so as to increase the useful travel of movable clamp 3 as illustrated in FIG. 2a.

Covers 10, 14 respectively are anchored on bases 9, 12 of clamps 4, 3 by means of corresponding locking screws 11, 15 which have recessed hexagonal heads.

In accordance with the invention, adjustment screw 6 is immobilized axially with respect to elongated body 2 by an axial immobilizing means comprising at least one smooth gauged pin, e.g., 16, which is inserted in a transverse hole in the body 2 and is designed to engage tangentially with a circumferential or circular recess or groove 17 having a semi-circular cross-section formed in the head of adjustment screw 6 allowing it to rotate about its longitudinal axis L.

Preferably two pins 16, 16.1 are provided on opposite sides of head 7 of adjustment screw 6 in a substantially symmetrical arrangement relative to axis L.

As a result of the substantial force exerted by pins 16, 16.1, screw 6 is axially immobilized in an extremely secure and reliable way and without any risk of breakage even when very high stresses are applied. That is, pins 16, 16.1 are able to resist substantial forces tending to cause displacement of screw 6 relative to body 2 in a direction parallel to axis L. Furthermore, given the fact that the key 13 and pins 16, 16.1 are made to dimensions with extremely small tolerances, the play in the rotatable coupling is reduced to a minimum, thus allowing micrometer adjustment of the movement of the clamp 3.

In order to increase the flexibility with which the clamps 3, 4 can be used, three transverse seats (e.g., 18, 19, 20) for the same number of bone bolts are provided on each of these instead of the two normally present in clamps used for grasping bone bolts.

For simplicity only the seats in clamp 3 will be described below, it being understood that the seats in clamp 4 are identical.

Three transverse grooves which are parallel to each other, indicated respectively by 18, 19, 20, are provided on the upper face of base 12 of clamp 3, while a similar number of grooves 21, 22, 23 are provided in cover 14 in corresponding positions. When the two sets of grooves 18, 19, 20, 21, 22, 23 are coupled together, the transverse cross-section resulting from the seats for the bolts is approximately elliptical and not circular, in order to provide secure immobilization of bone bolts of different diameters of, for example, 2 millimeters (mm) and 5 mm.

Additionally, the spacing a between grooves 18 and 19, or between grooves 21 and 22, on the same side of locking screw 15, is equal to approximately half the distance b between grooves 19 and 20, or between grooves 22 and 23, on the opposite side with respect to screw 15, so that three different spacings are possible. For example, if distance a is 4 mm and distance b is 8 mm, two bone bolts can be fitted with spacings of 4 mm, 8 mm or 12 mm.

It is desirable that a cylindrical insert 24 of elastomer material for example Teflon®, having a central hole for adjustment screw 6 and having an internal diameter which is slightly less than the external diameter of screw 6 is provided in the lower part of key 13 of movable clamp 3 to exert an anti-loosening braking effect on the latter. Insert 24 is coaxially lodged in an annular groove formed on the inner surface of the threaded hole in key 13 inwardly of the ends of the hole. The central hole of insert 24 may have the same diameter as the threaded hole in key 13.

A further clamp for transverse bone bolts anchored to body 2 at the end adjacent to fixed clamp 4 may also be provided, as indicated in general by reference number 25.

In particular, clamp 25 may comprise a forked stirrup 26 with an approximately U-shaped transverse cross-section with three pairs of opposing grooves provided on the inner faces of the stirrup to hold the bone bolts. The stirrup 26 may be anchored to the end face of base 9 of body 2 by means of a screw 27 which is also used to tighten the opposing faces of the stirrup against the bone bolts.

FIGS. 3 and 4 illustrate an articulated minisplint indicated generally by 1'. Parts in FIGS. 3 and 4 designated by reference numerals having a prime (') correspond to parts in FIGS. 1 and 2 having the same reference numerals but without the prime ('). Minisplint 1' comprises an elongated body 2' in the shape of a parallelepiped-bar having a rectangular cross-section, connected to an arm 28 by means of an axial joint which is indicated generally by reference number 29. Elongated body 2' has a longitudinal groove 5' and an adjustment screw 6' which is axially immobilized by means of a pair of keys 16', 16.1'. Arm 28 has an integral extension 9' which forms the base of clamp 4'.

In particular, axial joint 29 is formed of a pair of eyes 30 between which the end of arm 28 is inserted. The two parts, arm 28 and body 2', are hinged together by means of a pin 31 whose axis H is substantially parallel to the seats 9', 12' of the clamps 4', 3' of the bone bolts.

Desirably, pin 31 has a head 32 with a hexagonal recess, a smooth central portion 33 and a threaded end 34 onto which is screwed a lock nut 35. Thus, the pin 31 can be unscrewed and its position reversed to reduce the size of the joint 29 on the side adjacent to the bone, thus making the fixation right-handed or left-handed according to requirements.

Articulated minisplint or fixator 1" shown in FIGS. 5 and 6 differs from that in FIGS. 3 and 4 essentially in the fact that the axis V of axial joint 36 between elongated body 2" and arm 37 is substantially perpendicular to the seats of the clamps 3", 4" for the bone bolts. Parts in FIGS. 5 and 6 designated by reference numerals having a double-prime (") correspond to parts in FIGS. 3 and 4 having the same reference numerals but with a single-prime ('). Body 2" slidably supports clamp 3" which can move via an adjustment screw 6" which is axially immobilized by means of a pair of gauged pins 16", 16.1".

Figure 8:
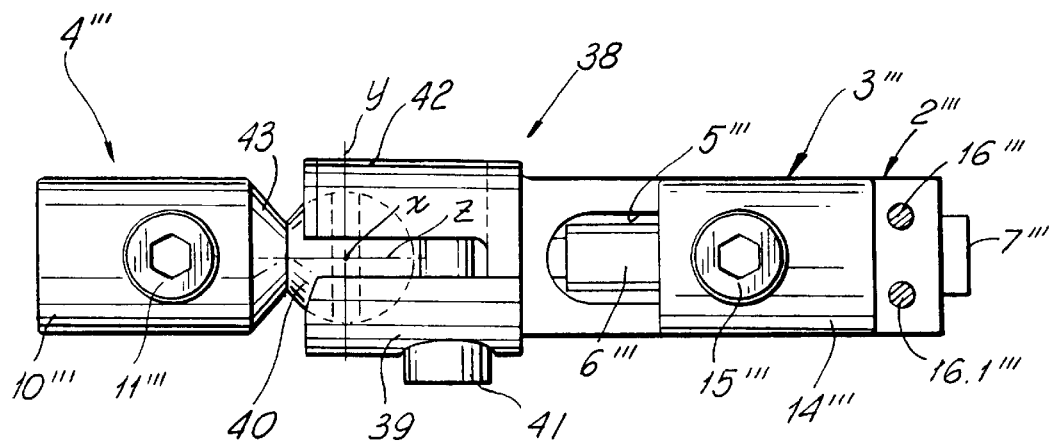
FIG. 8 shows a view from above of the minisplint device in FIG. 7.

Articulated minisplint 1''' illustrated in FIGS. 7 and 8 differs from those in FIGS. 3 to 6 in that connecting joint 38 comprises a pair of jaws 39, 42 with a hemispherical cavity for a ball 40 formed on arm 43 connected to base 9''' of clamp 4'''. Parts in FIGS. 7 and 8 designated by reference numerals having three primes (''') correspond to parts in FIGS. 3 and 4, and FIGS. 5 and 6 having the same reference numerals but with a single-prime (') and double-prime ("), respectively. The opening defined by jaws 39, 42 through which the portion of ball 40 contiguous with arm 43 extends is generally circular to allow pivoting of arm 43 about axis X (i.e. in the horizontal plane in FIG. 7), about axis Y (i.e., in the vertical plane in FIG. 7) or in planes therebetween. Lodging of ball 40 in the hemispherical cavity between jaws 39, 42 also allows pivoting or twisting of arm 43 about axis Z in FIG. 7. Jaws 39, 42 can be tightened against ball 40 by means of a locking screw 41 so as to lock the orientation of clamp 4'''.

The clamp 4''' is shaped in such a way (i.e., by arm 43 being integral with an end edge of base 9''') that the seats of clamp 4''' for the bone bolts F''' are located in a plane which is substantially parallel to the plane containing the seats of clamp 3''' when clamp 4''' is located in its outermost position relative to clamp 3''', i.e., when minisplint 1" is in a substantially straight condition as shown in FIG. 7. The portions of the interior surfaces of bases 9''', 12''' on which bone bolts F''' are seated are substantially flat, and the interior surfaces each have an integral boss through which locking screws 11''', 15''' extend.

Figure 9:
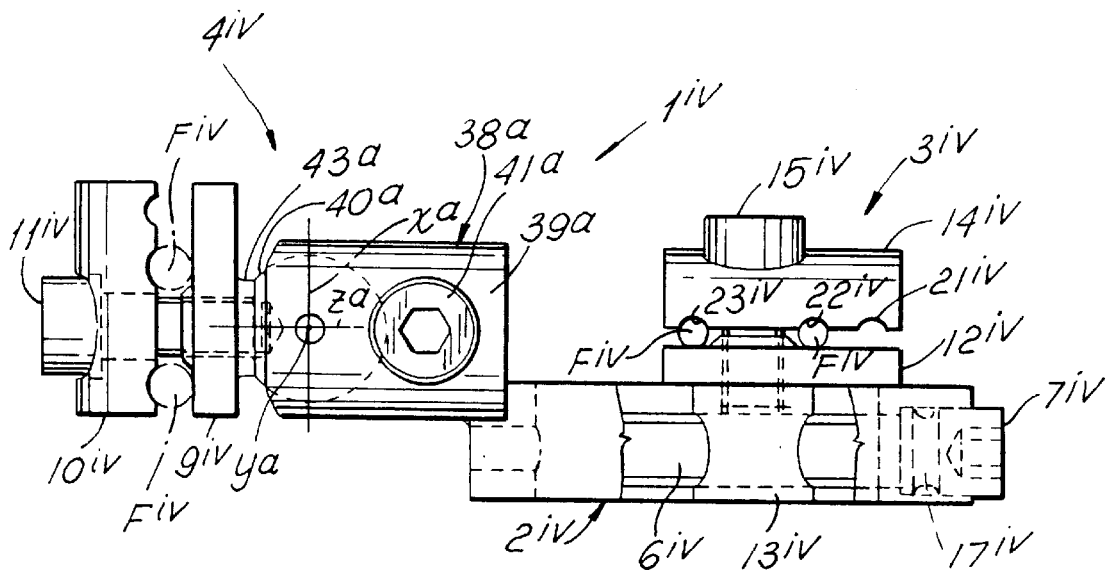
FIG. 9 shows a side view of a fourth embodiment of the minisplint device according to the invention.
Figure 10:
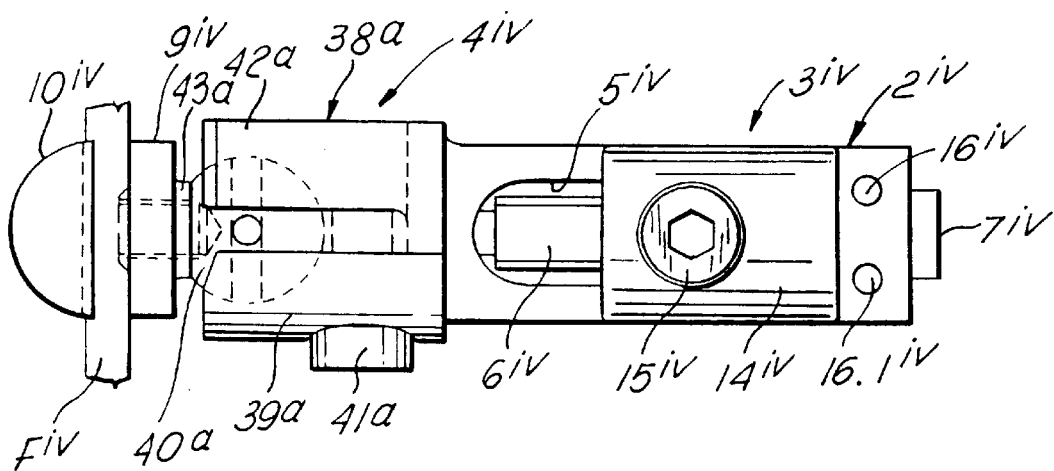
FIG. 10 shows a view from above of the minisplint device in FIG. 9.

Spherical joint minisplint device $1^{iv}$ illustrated in FIGS. 9 and 10 differs from that in FIGS. 7 and 8 essentially in the fact that the seats of clamp $4^{iv}$ for the bone bolts $F^{iv}$ are located in a plane which is substantially perpendicular to the plane containing the seats of clamp $3^{iv}$ when clamp $4^{iv}$ is located in its outermost position relative to clamp $3^{iv}$, i.e., when minisplint $1^{iv}$ is in substantially straight condition as shown in FIG. 9. This results from arm $43^a$ being integral with the surface of base $9^{iv}$ opposite the surface on which bone bolts $F^{iv}$ are seated which gives clamp $4^{iv}$ a "T"-configuration. Parts in FIGS. 9 and 10 designated by reference numerals having the superscript ($^{iv}$) correspond to parts in FIGS. 7 and 8 having the same reference numerals but with triple-primes ('''). Parts in FIGS. 9 and 10 designated by reference numerals having a superscript ($^a$) correspond to parts in FIGS. 7 and 8 having the same reference numerals but without any superscript.

The portions of the interior surfaces of bases $9^{iv}$, $12^{iv}$ on which bone bolts $F^{iv}$ are seated are substantially flat, and the interior surfaces each have an integral boss through which locking screws $11^{iv}$, $15^{iv}$ extend.

FIGS. 11 and 12 illustrate an articulated minisplint device indicated generally by reference number 100 which comprises two elongated bodies 101, 102 defined by parallelepiped-bars of slightly different lengths which slidably support clamps 103, 104 which can be moved along longitudinal grooves 105, 106 by means of corresponding adjusting screws 107, 108. Adjustment screws 107, 108 are also axially immobilized against the corresponding bars 101, 102 by means of smooth gauged pins 109, 109.1, 110, 110.1 which act together with circumferential grooves made in heads 111, 112 of the screws 107, 108.

The portions of the interior surfaces of bases 126, 127 on which bone bolts F1 are seated are substantially flat, and the interior surfaces each have an integral boss through which locking screws 130, 131 extend.

The two elongated bodies 101, 102 are joined together by means of a joint 113 whose axis K is substantially parallel to the seats of the clamps 103, 104 for the bone bolts F1.

For accurate and micrometer adjustment of the angle β formed between the two bodies 101, 102 there is provided an actuator 114 having screws 120, 121 with opposing threads acting on the ends of the bars 101, 102 adjacent to joint 113.

In particular, the actuator 114 essentially provides two elongate housings comprising stirrups or forks 115, 116 formed towards the adjacent ends of bodies 101, 102 which are capable of housing corresponding cylindrical blocks 117, 118 for rotation about respective central axes of the bodies 101, 102 which are transverse to the longitudinal central axes of the corresponding cylindrical blocks. Cylindrical blocks 117, 118 are rotatably fixed relative to the corresponding forks 115, 116 about the longitudinal central axes of the cylindrical blocks.

Screw 119 is defined by a cylindrical bar having ends 120, 121 which are externally threaded in opposite directions (i.e., right- and left-handed) and which engage corresponding holes with opposing threads in cylindrical blocks 117, 118. For example, screw 119 also has a central cylindrical expansion 122 with transverse holes 123 for the introduction of an adjustment key. By rotating oppositely threaded bars 120, 121 of screw 119 of actuator 114, pairs of stirrups 115, 116 are caused to move together or move apart in a direction parallel to the longitudinal axis of the threaded bars 120, 121 with a consequent micrometric change in the angle β formed between the two elongated bodies 101, 102. Such relative movement of stirrups 112, 113, and concomitant pivoting of about axis K, alters the angle between the stirrups and screw 119 which is permitted by the allowed rotation of cylindrical blocks 117, 118 about their respective transverse central axes.

In use, all that is necessary is to insert the bone bolts F, F', F'', F''', $F^{iv}$, F1, or Kirschner wires into the bone stumps at suitable distances corresponding to the spacings between the clamps 3, 4; 3', 4'; 3", 4"; 3''', 4'''; $3^{iv}$, $4^{iv}$, and then immobilize the clamps on the free ends of the bone bolts and finally bring about longitudinal movement of the clamps, via longitudinal guide means 5, 5', 5", 5'", 5$^{iv}$, 105, 106, and positioning of the elongated bodies and arms supporting the clamps, via axial joints 29, 36, connecting joints 38, 38$^a$, and joint 113, so as to set the fracture or correct deformation.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. An external minisplint device, comprising an elongated body which supports at least one pair of clamps each of which is capable of securing at least one pair of transverse bone bolts, longitudinal guide means associated with the said elongated body to guide the longitudinal translation movement of at least one of said clamps, at least one longitudinal adjusting screw which can rotate within said elongated body and engages a corresponding threaded hole formed in said movable clamp to position it selectively along said longitudinal guide means, said screw having a head which partly projects from one end of said elongated body and means for axially immobilizing said adjustment screw in its rotation, characterized in that said axial immobilizing means comprises at least one smooth elongated key in tangential contact with the base of a circular groove formed in said adjustment screw.

2. A minisplint device according to claim 1, in which said circular groove is formed in the head of said adjustment screw.

3. A minisplint device according to claim 1, in which said axial immobilizing means comprise a pair of smooth transverse pins which are substantially parallel and placed on opposite sides of said adjustment screw.

4. A minisplint device according to claim 1, in which each clamp comprises a base and a cover which can be coupled together by means of a locking screw and which are provided with corresponding transverse seats for at least three longitudinally offset bone bolts, the said seats having an approximately semi-elliptical transverse cross-section so as to receive bone bolts of different diameters.

5. A minisplint device according to claim 4, in which one of said seats is placed on the side opposite the other two with respect to said locking screw, with the spacing between the two seats on the same side being less than the spacing between the two seats on the opposite side with respect to the locking screw.

6. A minisplint device according to claim 1, the base of each movable clamp having on the underside a key which can slide in a correspondingly shaped longitudinal groove formed in said support and forming said guide means.

7. A minisplint device according to claim 6, in which said key has a rounded end of a shape complementing the ends of said longitudinal groove so as to increase the useful travel of the movable clamp.

8. A minisplint device according to claim 6, in which said threaded hole is made in said key, and in which said key houses an insert of elastomer material with a central hole of diameter slightly less than that of said adjustment screw to exert an anti-loosening braking effect on the latter.

9. A minisplint device according to claim 1, in which said support comprises a single-piece bar of substantially rectangular shape at one end of which there is formed as an integral piece the fixed base of one of said clamps.

10. A minisplint device according to claim 9, in which the outer face of said integral base has movable anchorage means for an additional clamp for transverse bolts.

11. A minisplint device according to claim 10, in which said additional clamp comprises a U-shaped stirrup with seats for bolts substantially perpendicular to the longitudinal axis of the support, in which the opposing faces of said stirrup can be moved towards the outer face of said integral base by means of a locking screw.

12. A minisplint device according to claim 9, in which the base of one of said clamps is connected to one end of said bar by means of a spherical joint provided with locking means to orient the clamp in a predetermined direction.

13. A minisplint device according to claim 1, in which said support is formed of two bars which are articulated together by means of an axial joint with a transverse axis, said bars being provided with corresponding longitudinal guide means.

14. A minisplint device according to claim 13, in which the ends of the end bars adjacent to said joint are connected by an actuator with counterthreaded screws to adjust the angle of inclination of said bars in a longitudinal plane perpendicular to the axis of the joint.

15. A minisplint device according to claim 13, in which said axial joint has a pin which can be removably inserted between the sides with respect to the midline of the joint in order to permit the device to be fitted bilaterally relative to a bone.

16. An external minisplint device comprising:

a clamp for grasping bone bolts, said clamp having an internally threaded hole;

an elongate body including a longitudinal guide means on which said clamp is mounted, said longitudinal guide means allowing translation of said clamp relative to said body in a direction parallel to the longitudinal axis of said body and obstructing translation of said clamp relative to said body in a direction perpendicular to said longitudinal axis;

an externally threaded adjustment screw extending through said body and internally threaded hole of said clamp such that the longitudinal axes of said adjustment screw and body are parallel, said threads of said adjustment screw corresponding to said threads of said hole in said base such that rotation of said adjustment screw produces concomitant longitudinal translation of said clamp relative to said body, said adjustment screw having a circular groove on its outer surface outside of the portion of said screw on which said clamp rides during said longitudinal translation; and an axial immobilizing means positioned in said circular groove between said adjustment screw and body to obstruct translation of said screw relative to said body in a direction parallel to said longitudinal axis and to allow rotation of said screw about its longitudinal axis relative to said body.

17. An external minisplint device according to claim 16 wherein said body has an elongate recess contained in a transverse plane relative to said longitudinal axis of said body, said elongate recess intersecting said circular groove tangentially relative to said adjustment screw, said axial immobilizing means comprising an elongate member having a cross section corresponding to that of said elongate recess positioned in said elongate recess tangentially relative to said adjustment screw.

18. An external minisplint device according to claim 16 wherein said elongate body and clamp constitute a first body and clamp, and further comprising a second elongate body hinged to said first elongate body for pivoting about a pivot axis, said second body carrying a second clamp for grasping bone screws, said first and second bodies each having a fixed elongate housing, said elongate housings being eccentrically located relative to said pivot axis, said elongate housings each supporting a respective block having an internally threaded bore, the longitudinal central axes of said bores being contained in a plane transverse to said pivot axis, each said block being rotatable about a central axis parallel to said pivot axis and rotatably fixed about the longitudinal central axis of said internally threaded bore, and an actuator screw having opposing externally counter-threaded portions extending through said internally threaded bores of said blocks, said external threads of said actuator screw complementing said internal threads of said blocks such that rotation of said actuator screw causes translation of said blocks relative to said screw and rotation of said blocks about an axis parallel to said pivot axis such that said bodies pivot relative to one another about said pivot axis.

19. An external minisplint device comprising:

a clamp having a depending slide-flange the longitudinal ends of which are curved in a plane which is perpendicular to said depending direction, said curvature being symmetric relative to the longitudinal central axis of said slide-flange;

an elongate body including a longitudinal groove into which said slide-flange extends when said clamp is mounted on said body to allow translation of said clamp relative to said body in a direction parallel to the longitudinal axis of said groove and obstruct translation of said clamp relative to said body in a direction perpendicular to said longitudinal axis of said groove, the ends of said longitudinal groove being curved to complement the curvature of said ends of said slide-flange; and adjustment means engaged with said clamp and body for longitudinally translating said clamp relative to said body when said slide-flange is inserted into said groove, said complementing curvatures of said slide-flange and said groove providing flush engagement between said slide-flange and the ends of said groove to increase the longitudinal displacement of said clamp relative to said groove.

20. An external minisplint device according to claim 19 wherein the portion of said clamp adjacent to said slide-flange comprises a base, said clamp further comprising a cover for clamping a plurality of bone bolts between it and said base, at least one of the surfaces of said cover and base against which the bone bolts are clamped having three elongate grooves each having a semi-elliptical cross-section and a longitudinal central axis parallel to the longitudinal central axes of the other two elongate grooves, the outer grooves being spaced asymmetrically relative to the central groove.

* * * * *